United States Patent [19]
Li

[11] Patent Number: 5,191,128
[45] Date of Patent: Mar. 2, 1993

[54] PROCESS FOR PREPARING TETRAPHENOLIC COMPOUNDS

[75] Inventor: Simon M. Li, Houston, Tex.

[73] Assignee: Shell Oil Company, Houston, Tex.

[21] Appl. No.: 851,376

[22] Filed: Mar. 12, 1992

[51] Int. Cl.$^5$ .................... C07C 39/12; C07C 37/20
[52] U.S. Cl. .................... 568/720; 568/722; 568/727
[58] Field of Search .................... 568/720, 722, 727

[56] References Cited

U.S. PATENT DOCUMENTS

| | | | |
|---|---|---|---|
| 3,013,087 | 12/1961 | Schwarzer | 260/619 |
| 3,049,569 | 8/1962 | Apel | 260/619 |
| 3,836,590 | 9/1974 | Brindell et al. | 568/720 |
| 4,415,725 | 11/1983 | Hedges et al. | 568/720 |
| 4,820,740 | 4/1989 | Li | 521/32 |
| 5,012,016 | 4/1991 | Li | 568/720 |

FOREIGN PATENT DOCUMENTS

| | | | |
|---|---|---|---|
| 57-38814 | 3/1982 | Japan. | |
| 859456 | 1/1961 | United Kingdom | 568/720 |

Primary Examiner—Werren B. Lone

[57] ABSTRACT

Tetraphenolic compounds such as the tetraphenol of ethane and the tetraphenol of xylene can be prepared in a ketone/alcohol solvent medium using a cation exchange resin catalyst.

16 Claims, 1 Drawing Sheet

PROCESS FOR PREPARING TETRAPHENOLIC COMPOUNDS

BACKGROUND OF THE INVENTION

This invention relates to the preparation of tetraphenolic compounds. In one aspect, the invention relates to a process for the continuous preparation of a tetraphenolic compound in a heterogeneous reaction mixture. In a specific embodiment, the invention relates to the continuous catalytic preparation of the tetraphenol of xylene from terephthalaldehyde and phenol.

Tetraphenolic compounds such as the tetraphenols of ethane and xylene are starting materials for the preparation of multifunctional epoxy resins for coatings and electronics applications. The tetraphenol of ethane, for example, can be prepared by the acid-catalyzed condensation reaction of glyoxal and phenol in a homogeneous liquid reaction mixture. Typical acid catalysts include aqueous hydrochloric acid and oxalic acid. When aqueous HCl is the catalyst for the reaction, it is typical to neutralize the acidic reaction product mixture by addition of a base such as sodium bicarbonate. The neutralized product mixture is then distilled for removal of excess phenol and by-products. The product yield of such a process is typically low, and the product is often contaminated with by-product from the sodium neutralizing agent. Use of strong acids also requires the use of special equipment including a glass-lined reactor, adding to the expense of the process.

It is therefore an object of the invention to provide a process for preparing tetraphenolic compounds. In one aspect, it is an object of the invention to provide a cation exchange resin-catalyzed process for preparing a tetraphenolic compound. In a further aspect, it is an object of the invention to improve product yield and reaction rate in the preparation of the tetraphenol of xylene.

SUMMARY OF THE INVENTION

According to the invention, a process is provided for preparing a tetraphenolic compound which can be described by the formula

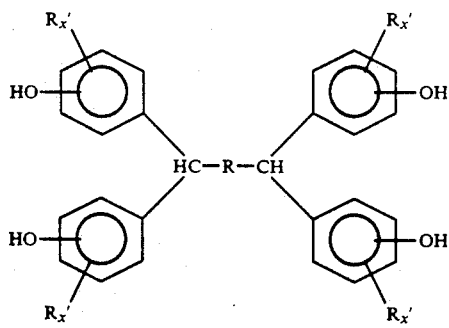

by contacting, in a solvent medium comprising a ketone and an alcohol, a dialdehyde with an equivalent excess of phenol in the presence of a cationic exchange resin catalyst. The use of a ketone/alcohol solvent mixture maintains the product tetrakisphenol in solution and accelerates the reaction to a high conversion of dialdehyde.

DETAILED DESCRIPTION OF THE INVENTION

Figure 1:
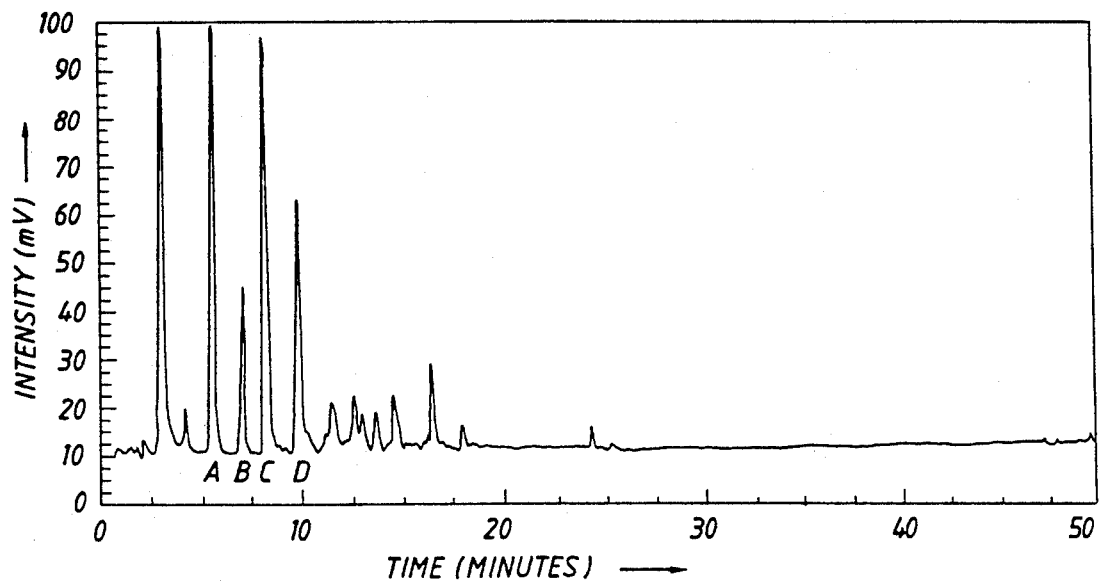
FIG. 1 is a high-performance liquid chromatogram (HPLC) of the product of the cation exchange resin-catalyzed reaction of phenol and terephthalaldehyde in methyl isobutyl ketone solvent.

The starting materials for the condensation reaction in the preparation of a tetraphenolic compound are a dialdehyde and a phenolic compound. Suitable dialdehydes include compounds which can be represented by formula (1):

in which R is a direct bond or a hydrocarbyl linking moiety. R can be, for example, $C_{1-20}$ hydrocarbyl, including unsubstituted and non-interfering substituted alkyl, aryl, alkaryl, aralkyl, cycloalkyl, and the like. Preferably, R is substituted or unsubstituted $C_{0-12}$ alkyl, aryl or alkaryl, particularly as represented structurally in formulas (2) and (3) below:

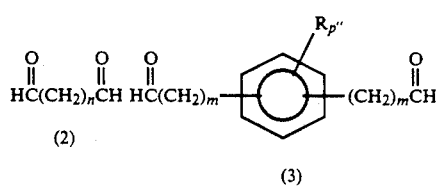

in which n is an integer from 0 to 12, m is an integer from 0 to 6, R" is a non-interfering substituent including $C_{1-4}$ alkyl and halide, and p is an integer from 0 to 4. Examples of such dialdehydes include glyoxal, glutaraldehyde, isophthalaldehyde and terephthalaldehyde.

The phenolic compound can be represented by formula (4):

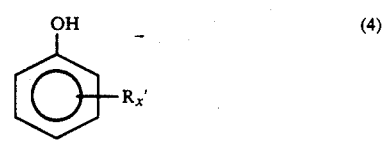

in which R can be any substituent which does not interfere with the condensation reaction, including $C_{1-6}$ alkyl and halide, for example, and x is an integer from 0 to 5. Examples of such phenols include phenol, chlorophenol, fluorophenol and cresol.

The dialdehyde and the phenol are contacted in a reaction medium which includes an excess of phenol. Generally, the starting reaction medium will contain an equivalent ratio of phenol to dialdehyde of at least about 8:1, preferably within the range of about 8:1 to about 25:1, most preferably about 10:1 to about 15:1. The excess phenol will generally serve as a reaction diluent, the amount of which can be adjusted depending upon the quantity of the organic cosolvents in the reaction mixture, and can be increased to help dilute the effect of excess water in the reaction mixture.

The dialdehyde and the phenol are reacted in the presence of an acidic cation exchange resin catalyst. A number of cation exchange resins having acid sites are known and commercially available. Preferable cation exchange resins are slightly-crosslinked (0–4%) sulfonated styrene/divinylbenzene copolymers. Cation exchange resins can include those which have a portion of the acid sites neutralized by mercaptoamine moieties such as those described in U.S. Pat. No. 3,394,089, U.S. Pat. No. 4,455,409 and U.S. Pat. No. 4,584,416, for example, although the unneutralized form is presently preferred for the preparation of tetraphenols. The presently preferred catalyst is a 2% divinylbenzene-crosslinked sulfonated polystyrene gellular resin. Such cation exchange resins are available from Rohm & Haas under the designation A-32 and from Bayer under the designation Lewatit SC-102, for example. Given the known sensitivity of such sulfonated ionic exchange resins to water (see, for example, U.S. Pat. No. 3,049,569, column 3, lines 52–59), it was surprising that they were effective in the synthesis of tetraphenols in reaction mixtures containing more than about 2 %w water. The amount of water in the reaction mixture is particularly high in the preparation of the tetraphenol of ethane, which starts with glyoxal, currently available as a 40 %w solution in water.

In the heterogeneous catalytic production of a tetraphenol, a dialdehyde, an excess of phenol and the solvent are fed to a reaction vessel containing the cation exchange resin catalyst. The reaction mixture is maintained at a temperature within the range of about 40° to about 110° C., preferably about 60° to about 95° C., for a time sufficient for preparation of the tetraphenol. The reaction is preferably carried out at atmospheric pressure. The reaction can be carried out in batch or continuous form. Under large-scale reaction conditions, continuous form will be preferred. The cation exchange resin catalyst can be used as a slurry with the reactants in batch reactions or in a fixed bed in a continuous process. Two or more staged additions of the dialdehyde with interstage water evaporation can be employed to enhance yields.

The reaction is carried out in an organic cosolvent medium comprising both a ketone and an alcohol. Such a solvent medium has been found to promote the solubility of the starting dialdehyde. Furthermore, in a continuous process, the presence of the ketone prevents premature precipitation of the product or product intermediates as they form, while the alkanol has been found to increase the rate of the reaction. The ketone component of the solvent can be, for example, acetone, methyl ethyl ketone, methyl isobutyl ketone, ethyl isobutyl ketone and diisobutyl ketone. Preferred are the hindered alkyl-substituted ketones such as methyl isobutyl ketone. The ketone will generally be present in the reaction mixture in an amount of about 5 to about 50 weight percent, preferably about 10 to about 40 weight percent, based on the weight of the total reaction mixture. Preferred alcohols, because of their availability and low cost, are $C_{1-8}$ alkanols such as methanol, isopropanol, ethanol and butanol, for example. The alcohol will generally be present in a molar ratio with respect to the dialdehyde of at least about 2:1, preferably within the range of about 2:1 to 15:1, most preferably about 4:1 to about 8:1. The currently preferred solvent mixture contains methanol and methyl isobutyl ketone.

The reaction time depends upon the reaction temperature and other reaction conditions. In a batch process, a reaction time within the range of about 0.1 to 20 hours will generally achieve desired conversion. In a continuous operation using a fixed catalyst bed, a flow rate with the range of about 0.1 to 12.0, preferably 0.5 to 8, weight per hour per bed weight will generally be suitable.

When the reaction is complete, the product solution is separated from the solid catalyst. The tetraphenol is recovered by means such as flash distillation to remove any cosolvent, excess phenol, by-product water and other volatile impurities, and steam-stripped to remove unwanted oligomers or isomers. Alternatively, a more selective product can be recovered by cooling a solution of the condensation product to crystallize a polyphenolic product relatively rich in the tetrakisphenol species. The crystallization medium can be the excess phenolic reactant or it can be an organic solvent. The tetraphenol can then be purified by subsequent steps such as recrystallization, solvent washing and the like. The product of the invention process will be a mixture of phenolic oligomers and isomers. A preferred technique for product recovery to maximize recovery of the tetraphenol product is to remove water, alcohol and ketone from the product mixture by distillation and then to cool the remaining solution to precipitate the tetraphenol. The phenol mother liquor from the precipitation step can then be recycled to the reaction mixture.

EXAMPLE 1

This example illustrates the batch preparation of the tetraphenol of xylene (TPX) using a cation exchange resin catalyst in the absence of an organic solvent.

151g of a 15:1 molar phenol/terephthalaldehyde (TDA) solution was charged to a flask equipped with a stirrer and condenser and heated to 80° C. Upon addition of 15g of vacuum-dried Lewatit ® SC-102 cation exchange resin (2% divinylbenzene-crosslinked sulfonated polystyrene), a significant exotherm was observed and controlled with air cooling. The color of the solution changed progressively from light yellow to burgundy with apparent increased solution viscosity. After about 2 hours, solids began forming in the solution phase at the reaction temperature, indicating that the product had exceeded its solubility in the reaction medium. The precipitate was confirmed by mass spectroscopy to be the tetrakisphenol of xylene.

EXAMPLE 2

This example illustrates the continuous preparation of TPX using a cation exchange resin catalyst in the presence of methanol and the absence of a ketone. A feed consisting of a 20:1 molar phenol/TDA solution and a methanol:TDA molar ratio of about 8:1 was pumped via a metering pump through a glass-jacketed fixed-bed reactor containing a 2% divinylbenzene-crosslinked sulfonated resin which had been conditioned with dry phenol. Reaction temperatures varied during the 2-week run between 65° and 80° C. As the continuous run progressed, a change in the appearance of the catalyst surface was observed. The run was terminated after product analysis showed markedly decreased conversion. Inspection of the catalyst led to the conclusion that product precipitating from the reaction mixture was coating the catalyst beads.

EXAMPLE 3

This example illustrates the continuous preparation of the tetraphenol of xylene in a solvent medium using a cationic exchange resin catalyst. A series of experiments was performed at various reaction temperatures and ratios of reactants at a phenol to terephthalaldehyde molar ratio of 20:1. Reactants were charged to a feed vessel and pumped via a metering pump through a fixed-bed reactor containing a 2% divinyl benzene-crosslinked sulfonated polystyrene resin which had been conditioned with dry phenol and MIBK. Samples of product were taken after steady-state had been reached. Conditions and results are summarized in Table 1.

TABLE 1

| Run Number | Continuous TPX Synthesis | | | | | | | | |
|---|---|---|---|---|---|---|---|---|---|
| | 1 | 2 | 3 | 4 | 5 | 6 | 7 | 8 | 9 |
| % w MIBK | 20.0 | 20.0 | 20.0 | 15.0 | 15.0 | 30.0 | 30.0 | 30.0 | 30.0 |
| MeOH/TDA, M/M | 0.0 | 0.0 | 0.0 | 0.0 | 4.0 | 12.0 | 12.0 | 6.0 | 6.0 |
| DP1*[1] | 0.46 | 0.34 | 1.05 | 1.49 | 0.25 | 0.02 | 0.02 | 0.11 | 0.02 |
| DP2* | 0.23 | 0.18 | 0.44 | 0.58 | 0.14 | — | 0.01 | 0.06 | 0.01 |
| TPX1* | 1.68 | 1.43 | 1.38 | 1.58 | 1.67 | 1.85 | 1.97 | 1.64 | 1.60 |
| TPX2* | | | | | 1.00 | | | | |
| TEMP, °C. | 75 | 85 | 85 | 75 | 75 | 65 | 65 | 65 | 75 |
| 1/WHSV[2], hr | 2 | 2 | 1.7 | 1.4 | 1.8 | 1.4 | 2.2 | 3.0 | 1.4 |

[1]These are areas relative to TPX2 as analyzed by HPLC; TPX1* = TPX1/TPX2, etc.
[2]WHSV = flow rate in wt/hr per catalyst weight.

In runs 1-4, carried out in the presence of MIBK solvent but without alcohol cosolvent, conversion of TDA into the desired TPX was relatively low and there were significant levels of the diphenolic isomers (represented as DP1 and DP2). In runs 5-9, the effect of added methanol on conversion to TPX isomers can be seen, suggesting that methanol is acting to accelerate the reaction.

Figure 2:
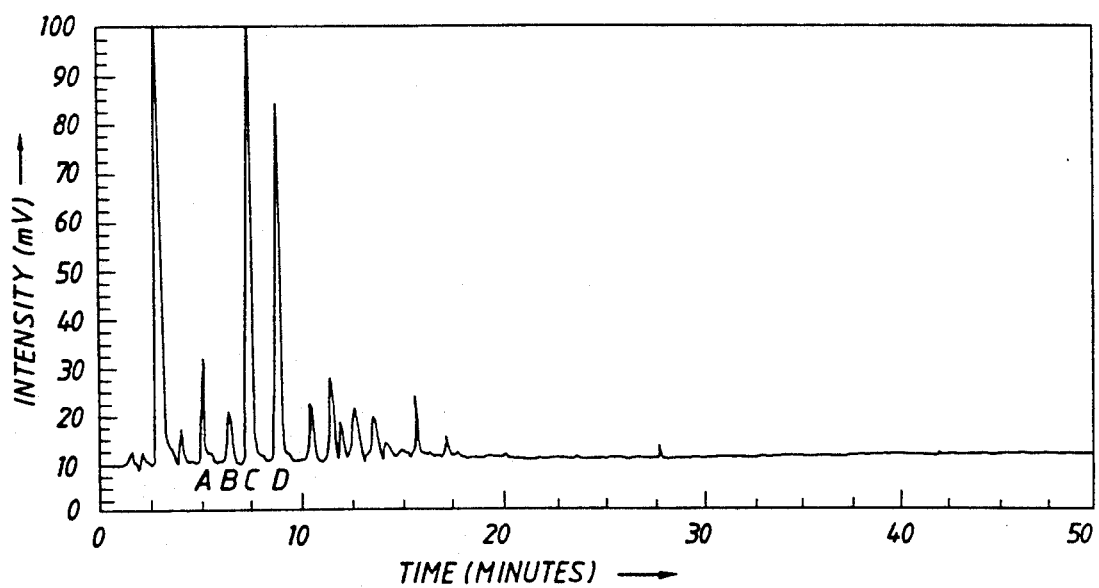
FIG. 2 is an HPLC of the product of the cation exchange resin-catalyzed reaction of phenol and terephthalaldehyde in a solvent mixture of methyl isobutyl ketone and methanol.

FIGS. 1 and 2 are HPLC's of the products of Runs 4 and 5, respectively. As can be seen from the chromatographs, the presence of both MIBK and methanol in the reaction medium resulted in a mixed reaction product relatively low in diphenolic intermediates (peaks A and B on each chart) and relatively high in the desired tetrakisphenolic species (peaks C and D on each chart).

I claim:
1. A process for preparing a tetraphenol of the formula

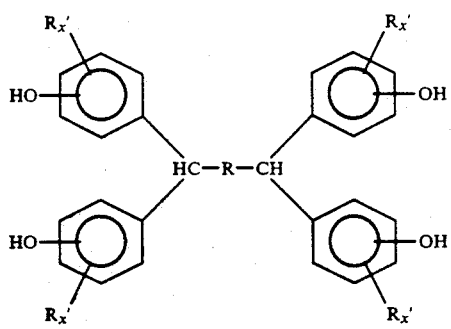

in which R is a direct bond or a hydrocarbyl linking moiety, R' is selected from the group consisting of $C_{1-6}$ alkyl and halide, and x is an integer from 0 to 5, the process comprising contacting, at a temperature within the range of about 40° to about 110° C. in a solvent medium comprising a ketone and a $C_{1-8}$ alkanol, a dialdehyde of the formula

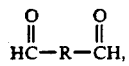

in which R is a direct bond or hydrocarbyl linking moiety, and a stoichiometric excess of a phenolic compound which can be represented by the formula

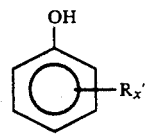

in the presence of a catalytic amount of an acid-functional cation exchange resin.

2. The process of claim 1 in which the dialdehyde can be represented by the formula

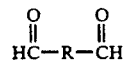

in which R is a direct bond or a substituted or unsubstituted $C_{1-20}$ hydrocarbyl.

3. The process of claim 2 in which the phenolic compound is phenol.

4. The process of claim 1 in which the solvent medium comprises methyl isobutyl ketone.

5. The process of claim 1 in which the solvent medium comprises methanol.

6. The process of claim 4 in which the phenol is present in a molar ratio to the dialdehyde of at least about 8:1.

7. The process of claim 4 in which the solvent medium comprises methanol.

8. The process of claim 1 in which the dialdehyde can be represented by the formula

in which n is an integer selected from 0-12.

9. The process of claim 8 in which the dialdehyde is glyoxal.

10. The process of claim 1 in which the dialdehyde can be represented by the formula

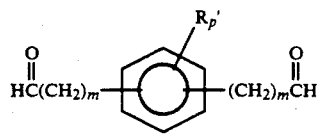

in which m is an integer within the range of 0 to 6, R' is a non-interfering substituent, and p is an integer from 0 to 4.

11. The process of claim 10 in which the phenolic compound is phenol and the aldehyde is terephthalaldehyde.

12. The process of claim 1 in which the ketone is present in the reaction mixture in an amount within the range of about 10 to about 40 weight percent based on the weight of the reaction mixture, and the alkanol is present in an amount of about 4 to about 8 moles per mole of the dialdehyde.

13. The process of claim 1 in which the cation exchange resin is a divinylbenzene-crosslinked sulfonated polystyrene ionic exchange resin.

14. The process of claim 14 in which the cation exchange resin has a degree of divinylbenzene crosslinking no greater than about 4%.

15. A process for preparing the tetraphenol of xylene comprising contacting, at a temperature within the range of about 40 to about 110° C. in a solvent medium comprising a ketone and a $C_{1-8}$ alkanol, phenol and terephthalaldehyde in a molar ratio within the range of about 8:1 to about 25:1 in the presence of a catalytic amount of an acid-functional cation exchange resin.

16. The process of claim 15 in which the ketone is methyl isobutyl ketone and the alkanol is methanol.

* * * * *